(12) United States Patent
Beneke

(10) Patent No.: US 7,062,074 B1
(45) Date of Patent: Jun. 13, 2006

(54) METHOD OF PROCESSING X-RAY IMAGES

(75) Inventor: Knut Beneke, Ober-Olm (DE)

(73) Assignee: Heimann Systems GmbH, Wiesbaden (DE)

( * ) Notice: Subject to any disclaimer, the term of this patent is extended or adjusted under 35 U.S.C. 154(b) by 0 days.

(21) Appl. No.: 09/537,546

(22) Filed: Mar. 30, 2000

(30) Foreign Application Priority Data

Apr. 14, 1999 (DE) ................................ 199 16 664

(51) Int. Cl.
*G06K 9/00* (2006.01)

(52) U.S. Cl. ..................................................... 382/123

(58) Field of Classification Search ................ 382/132, 382/131, 128, 129, 203, 173, 177, 180, 280, 382/283, 291
See application file for complete search history.

(56) References Cited

U.S. PATENT DOCUMENTS

| | | | | |
|---|---|---|---|---|
| 5,022,062 A | * | 6/1991 | Annis | 378/86 |
| 5,098,640 A | * | 3/1992 | Gozani et al. | 376/166 |
| 5,212,637 A | | 5/1993 | Saxena | |
| 5,544,256 A | | 8/1996 | Brecher et al. | |
| 5,594,768 A | * | 1/1997 | Fujii et al. | 378/21 |
| 5,712,926 A | * | 1/1998 | Eberhard et al. | 382/205 |
| 5,793,901 A | * | 8/1998 | Matsutake et al. | 382/294 |
| 5,807,256 A | | 9/1998 | Taguchi et al. | |
| 5,838,758 A | * | 11/1998 | Krug et al. | 378/53 |
| 5,905,806 A | * | 5/1999 | Eberhard et al. | 382/100 |
| 6,084,984 A | * | 7/2000 | Ishikawa | 382/294 |
| 6,230,174 B1 | * | 5/2001 | Berger et al. | 715/513 |
| 6,272,230 B1 | * | 8/2001 | Hiraoglu et al. | 382/100 |
| 6,317,509 B1 | * | 11/2001 | Simanovsky et al. | 382/131 |
| 6,473,487 B1 | * | 10/2002 | Le | 378/57 |

OTHER PUBLICATIONS

H. Brüning, S. Wolff: "Automated Explosive Detection Systems Based Upon CT Technology"; Proceedings of the 32$^{nd}$ Annual International Carnahan Conference on Security Technlogy, Oct. 1998; pp. 55-58.

* cited by examiner

*Primary Examiner*—Samir Ahmed
*Assistant Examiner*—Brain Le
(74) *Attorney, Agent, or Firm*—Venable LLP; Michael A. Sartori

(57) ABSTRACT

A method of processing an X-ray image of articles contained in a transilluminated object and made visible for an observer on a monitor screen, includes the following steps: Placing individual markings about the image of certain, previously determined articles and automatically and stepwise combining the individual markings into a final added marking if at least two individual markings mutually fit. The combining step includes the steps of comparing for fit mutually facing sides of two adjoining individual markings and determining a ratio of an overlapping area of the two adjoining individual markings to the total area of at least one of the two adjoining individual markings.

18 Claims, 4 Drawing Sheets

METHOD OF PROCESSING X-RAY IMAGES

CROSS REFERENCE TO RELATED APPLICATION

This application claims the priority of German Application No. 199 16 664.1 filed Apr. 14, 1999, which is incorporated herein by reference.

BACKGROUND OF THE INVENTION

This invention relates to a method of processing X-ray images. Articles contained in a transilluminated object are made visible to an operator/observer on a monitor and markings are placed around earlier-defined articles.

To facilitate the evaluation of an X-ray image of transilluminated objects for an observer, the X-ray image is automatically examined in the X-ray system based on various properties. In such an arrangements a software is used to search in the transilluminated object for certain previously defined articles such as firearms, piercing weapons or explosives.

A method of the above-outlined type is described in German Patent document 198 55 250.5. If such an article is detected, the observer receives information that the article in the transilluminated object has to be more thoroughly investigated. Such an information is the marking of the discovered article on the monitor, for example, by drawing a circle or frame therearound. Since the detected articles are not recognized as a whole, a marking is placed about each detected article. An evaluation by the observer is made difficult if a plurality of such markings appear on the monitor. Such an event is of significant disadvantage for the observer if the run-through period is, for example, approximately 6 seconds.

SUMMARY OF THE INVENTION

It is an object of the invention to provide an improved method of processing an X-ray image in which the placed markings are optimized to facilitate the evaluation of an X-ray image for the observer.

This object and others to become apparent as the specification progresses, are accomplished by the invention, according to which, briefly stated, the method of processing an X-ray image of articles contained in a transilluminated object and made visible for an observer on a monitor screen, includes the following steps: Placing individual markings about the image of certain, previously determined articles and automatically and stepwise combining the individual markings into a final added marking if at least two individual markings mutually fit. The combining step includes the steps of comparing for fit mutually facing sides of two adjoining individual markings and determining a ratio of an overlapping area of the two adjoining individual markings to the total area of at least one of the two adjoining individual markings.

The invention is based on the principle to automatically couple to one another the numerous visible markings, so that on the monitor only a single marking as the sum of the individual markings appears to thus provide for the observer a central marking to make possible a rapid and reliable evaluation concerning the article in the transilluminated object. The coupling of the markings is effected by a function which is inputted in the X-ray system and which combines the mutually fitting markings and places a combined marking into the X-ray image. Only markings which belong to one another are combined. Whether two markings belong to one another is determined by their spatial proximity and their overlap.

According to an advantageous feature of the invention, joined markings may again be removed, for example, when the operator wishes to see the markings individually. Also, the extent of the combination of the markings may be adjusted. As a result, the markings may be shown unchanged or combined. Further, intermediate steps are possible in which case then maximum 2, 3, 3, 5, etc. markings may be coupled to one another, so that on the monitor two to three markings, etc. may be made visible as individual added markings.

DESCRIPTION OF THE PREFERRED EMBODIMENT

Figure 1:
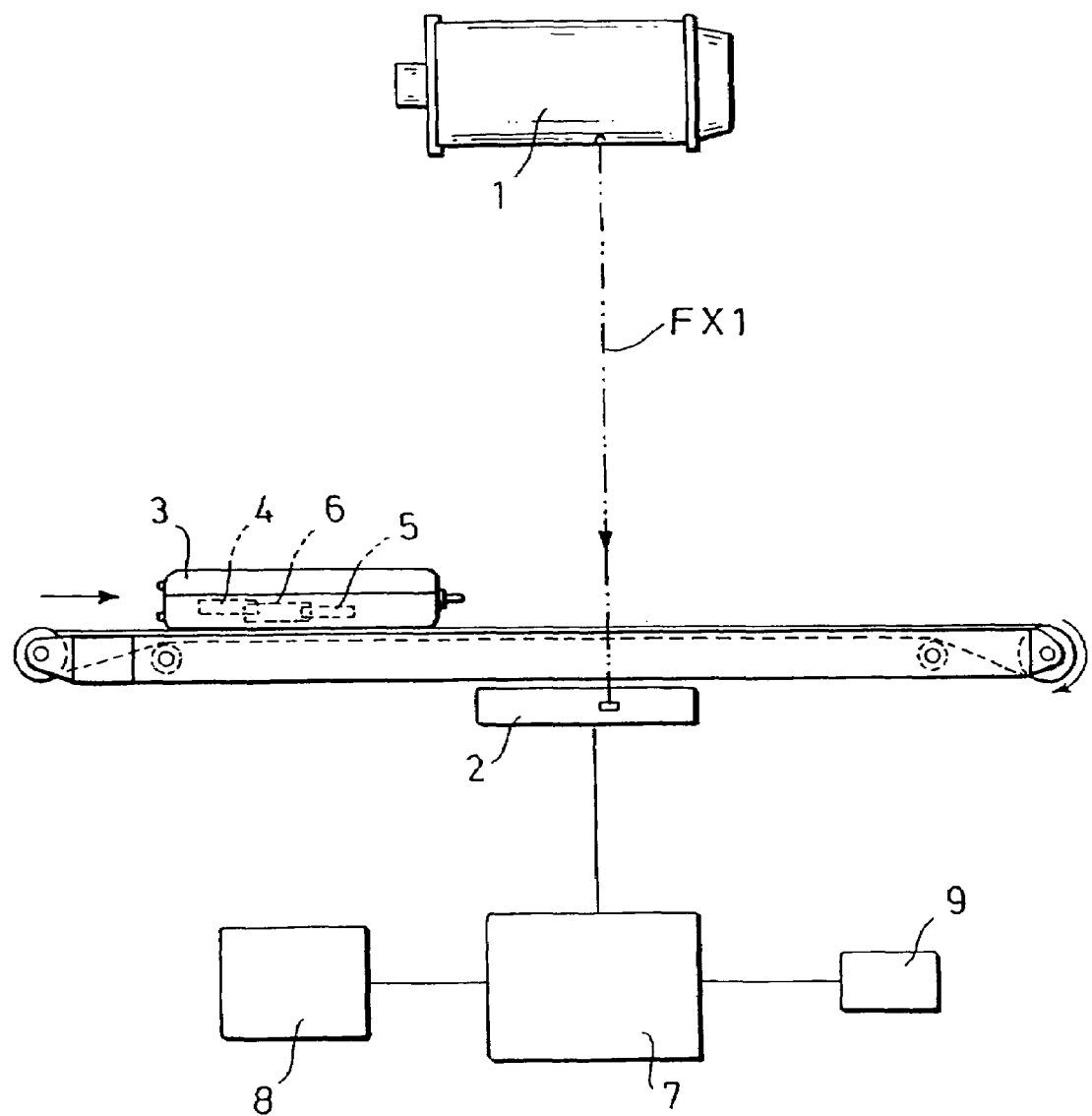
FIG. 1 is a simplified schematic illustration of an X-ray system adapted to perform the method according to the invention.

FIG. 1 illustrates an X-ray system having a conventional X-ray generator 1 and a detector 2, between which an object 3 to be transilluminated is positioned. The object 3 may be a piece of luggage in which various articles 4, 5, 6 are contained. Non-illustrated known components couple a computer system 7 with the detector 2. The measuring results are made visible on a monitor 8 and/or a printer 9 coupled to the computer system 7.

Figure 2:
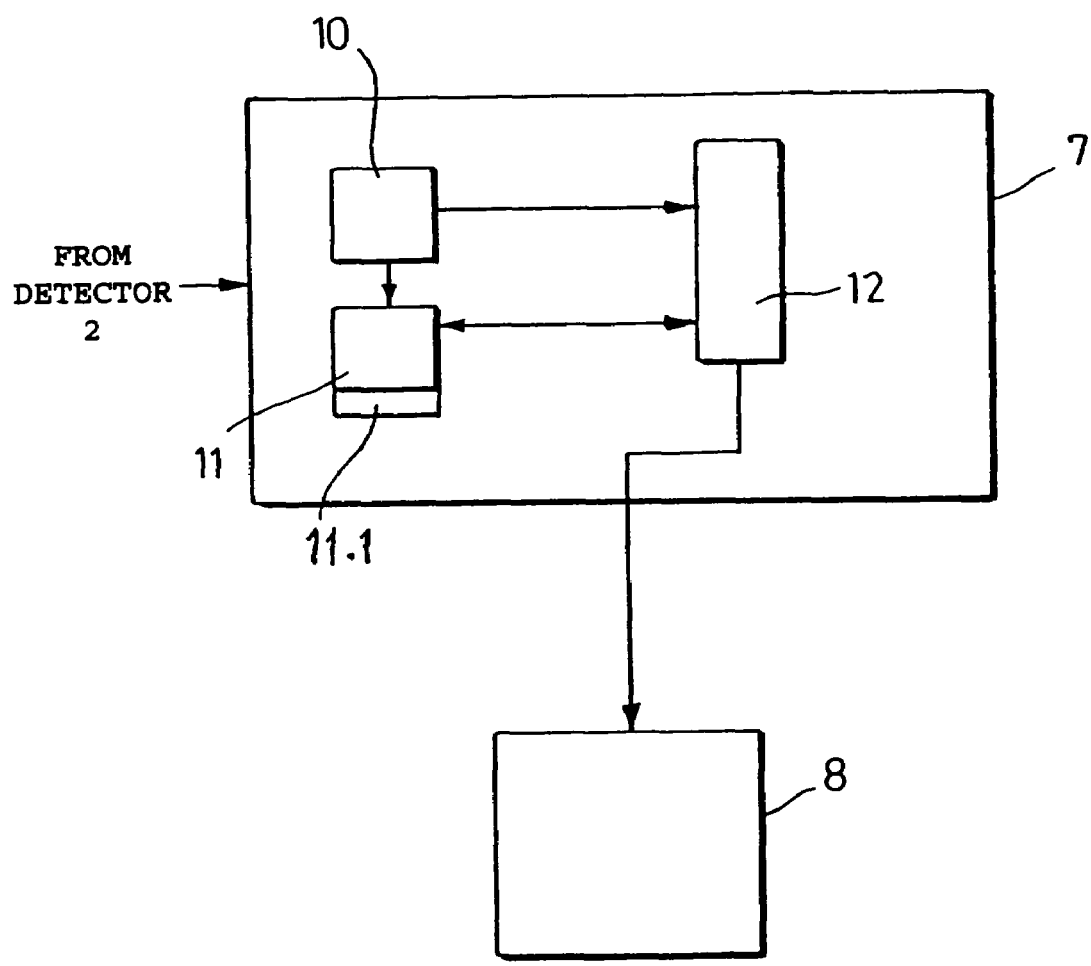
FIG. 2 is a block diagram of a computer system in an X-ray system for performing the method according to the invention.

FIG. 2 illustrates the essential component groups of the computer system 7 for performing the method according to the invention. The output of the detector 2 is connected with an image processing device 10 which is, in turn, connected with a marking memory 11 and a memory 12 for the marking lists. The marking memory 11 is bi-directionally connected with the memory 12 and thus gains access to the marking list accumulated during the process. The marking memory 11 is provided with a sub-marking memory 11.1 which will be described in more detail as the specification progresses.

The method according to the invention is performed as follows:

The X-ray generator 1 directs an X-ray beam FX1 to the object 3 to be transilluminated. The X-ray beam FX1 is weakened by the respective absorption behavior of the articles 4, 5, 6 in the object 3 as well as by the housing material of the object 3 and is received by the detector 2. The detector 2, for example, a line camera formed of a plurality of X-ray detectors, produces signals from the non-absorbed part of the X-ray beam and applies the signals, as image data information about the transilluminated object 3, to the computer system 7 for image processing. Such an inputting is performed preferably line-by-line and in a continuous manner. The image data are evaluated in a known manner in the image processing device 10 and are readied for a visual representation on a monitor. An X-ray image represented in this manner is composed of image dots having various properties, for example, a gray scale and material value from which the article 4, 5, 6 may be recognized.

Figure 3A:
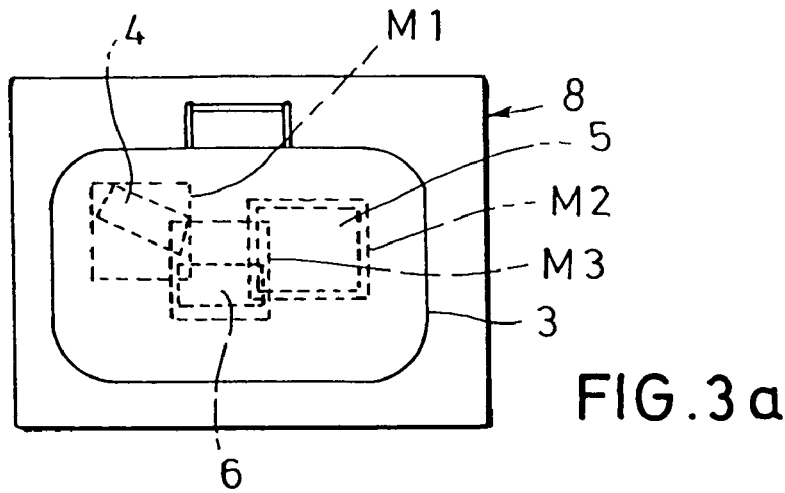
FIGS. 3a, 3b and 3c are visual representations for providing a common marking on the monitor.

In principle, about each detected article defined as dangerous, for example articles 4, 5, 6, automatically a respective separate individual marking M1, M2, M3 is placed, as shown in FIG. 3*a*. Thus, about the first-recognized article 4 the marking M1 and about the second-recognized article 5 a marking M2 is placed. Already at this point the two markings M1, M2 are compared with one another by means of a function to determine whether the two markings M1 and M2 fit to one another. For this purpose the mutually fitting or mutually facing sides of the markings M1 and M2 are compared by means of coordinate comparison. The more these sides correspond to one another in position and length, the better their fit. The distance between the individual markings M1 and M2 must not exceed a previously set, variable limit value.

In the present illustration the individual markings M1 and M2 are situated too far from one another so that no common marking is established. Both markings M1 and M2 are inputted into the list memory 12 as well as the sub-marking memory 11.1 of the marking memory 11.

Figure 3B:
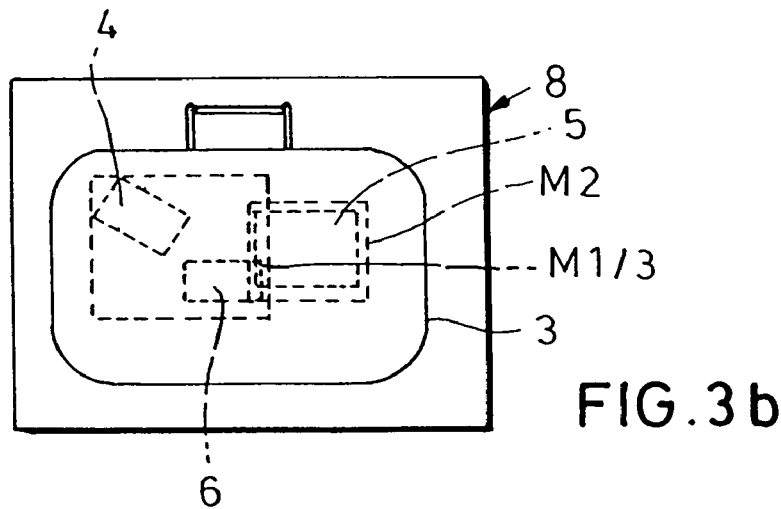

Approximately at the same time the detection of the article 6 and placing the marking M3 thereabout occur. In a further step the marking M3 is compared with the marking M1, that is, it is determined whether the individual markings M1 and M3 mutually fit. Since both markings M1 and M3 overlap on the fitting sides, additionally the ratio of the common (overlapping) surfaces of the two markings M1 and M3 to the surface of the smaller of the two markings M1 and M3 is determined for verifying the mutually fitting sides. The greater the ratio the better the mutual fit of the markings M1 and M3. As shown in FIG. 3*b*, the markings M1 and M3 are replaced by a new marking as an individual added marking M1/3 in which the respective outer sides of the markings M1 and M3 yield the size of the new individual added marking M1/3. To ensure that the individual markings M1 and M3 are not lost in the computer system, they are stored in the sub-marking memory 11.1 as sub-markings M1 and M3 of the individual added marking M1/3.

Figure 3C:
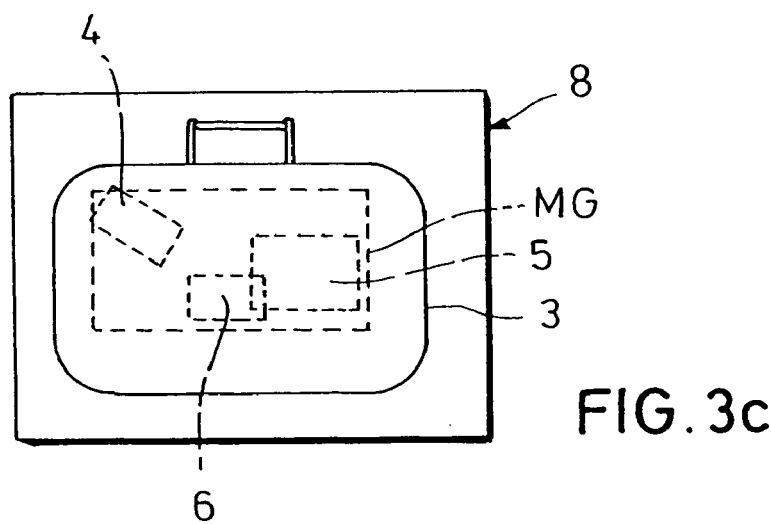

Approximately at the same time, the new individual added marking M1/3 is compared for correspondence with the individual marking M2 from the marking list. As a result of such a comparison, a new marking Mg as a final added marking is applied to the monitor 8. As shown in FIG. 3*c*, the articles 4, 5 and 7 are found within the final added marking Mg. The individual marking M2 and the individual added marking M1/3 become sub-markings of the final added marking Mg. Thus, for the observer there is obtained a well ascertainable X-ray image on the monitor 8 on which advantageously only a single final added marking Mg is shown without, however, losing the relationships between the individual markings M1, M2, M3 and the representation of the final added marking Mg on the monitor 8.

Figure 4A:
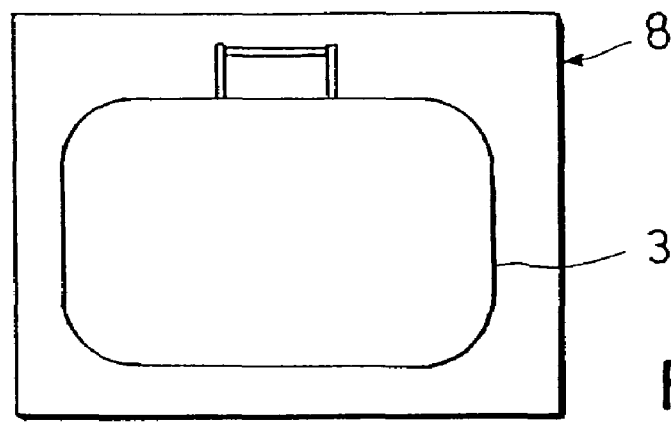
FIGS. 4a, 4b and 4c are visual representations of the method for removing the common marking from the monitor.
Figure 4B:
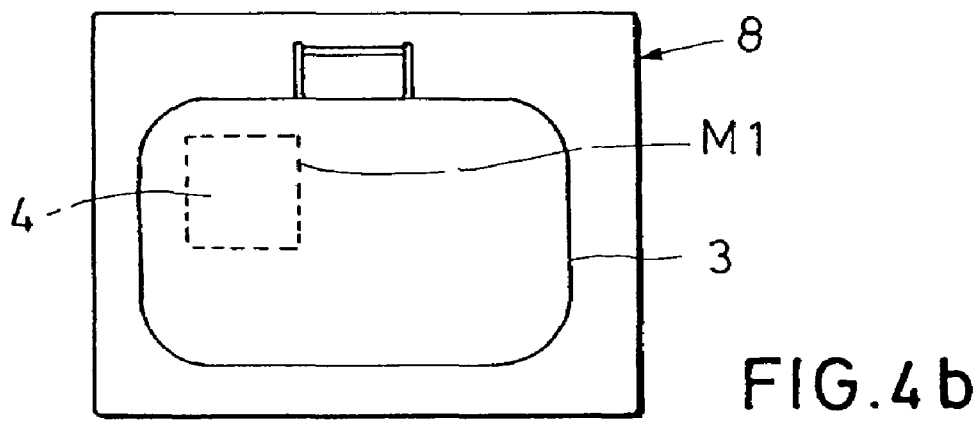
Figure 4C:
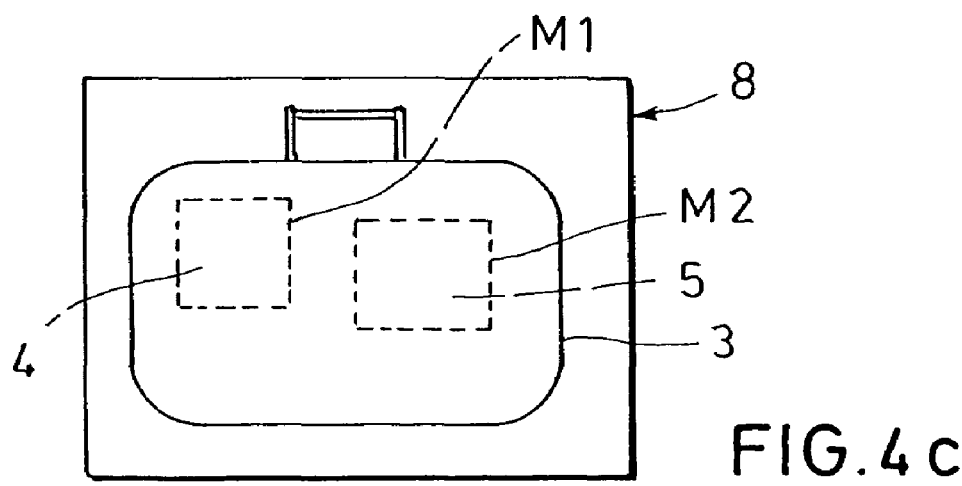

The information concerning the individual markings M1, M2, M3 as well as their assignment as sub-markings in relation to the individual added marking M1/3 and the final added marking Mg remain in the computer system 7 in the memory 12 as well as in the sub-marking memory 11.1. This makes it possible to again separately display, upon extinguishing the final added marking Mg, all sub-markings M1 and M3 of the individual added marking M1/3 as well as the sub-marking M2. For this purpose the final added marking Mg is removed by the operator from the monitor 8, for example, by pushbutton operation, whereupon the computer system 7 again renders visible the individual stored markings M1, M2 (M3 is not shown) on the monitor 8, as shown in FIGS. 4*a*, 4*b* and 4*c*.

Such necessary information is taken in steps from the sub-marking memory 11.1 as well as from the marking list in the memory 12. The computer system 7 proceeds with the earlier-described steps in a reverse order. First it is determined which final added marking Mg was removed and the sub-marking memory 11.1 is searched for the individual, associated sub-markings. In this proceeding the sub-marking M1/3 belonging to the final added marking Mg as well as the sub-marking M2 are found. The final added marking Mg is extinguished in the marking list and the sub-marking M1/3 found in the sub-marking memory 11.1 and the sub-marking M2 are added to the marking list of the memory 12. Further, by means of the software of the computer system 7 it is recognized that the sub-marking M1/3, as an individual added marking, is composed of the markings M1 and M3, while the sub-marking M2 has no further sub-markings and thus represents an individual marking. In the marking list the individual added marking M1/3 is extinguished and replaced by the sub-markings M1 and M3 which are then inputted from the sub-marking memory 11.1 in the memory 12. The individual markings M1, M2 and M3 are applied to the monitor 8 from the marking list and displayed thereon. In this manner the observer may decide whether the common marking Mg or the sub-markings/individual markings M1/3, M2 or only the individual markings M1, M2, M3, etc. should be shown on the monitor 8.

It is to be understood that upon detection of several articles, that is, more than the mentioned three articles 4, 5 and 6 the set markings M1, M2 and M3, etc. are compared with one another as long as no mutually fitting markings (individual added markings) are found.

Several variants are feasible within the scope of the invention. Thus, the degree and combination of the marking may be set. With such a setting it may be achieved that the markings are not always combined or are only partially combined, that is, intermediate steps with respect to the degree of combination are possible. In this manner too, individual markings may be removed from the combined markings which will thus decompose into several parts.

It will be understood that the above description of the present invention is susceptible to various modifications, changes and adaptations, and the same are intended to be comprehended within the meaning and range of equivalents of the appended claims.

What is claimed is:

1. A method of processing an X-ray image of articles contained in a transilluminated object and made visible for an observer on a monitor screen, comprising the following steps:
    (a) placing individual markings about the image of certain, previously determined articles; and
    (b) automatically and stepwise combining the individual markings into a final added marking if at least two individual markings mutually fit; and
    (c) storing said individual markings in a marking list of a memory; said combining step comprises the steps of
        (1) performing a coordinate comparison to identify mutually facing sides of two adjoining individual markings;
        (2) determining a ratio of an overlapping area of said two adjoining individual markings to the total area of at least one of said two adjoining individual markings;

(3) forming an individual added marking from two individual markings resulting from said comparing and determining steps;

(4) storing said individual added marking in said marking list;

(5) storing said individual markings, from which said individual added marking has been formed, from said marking list in a sub-marking memory of a marking memory as sub-markings of said individual added marking;

(6) comparing said individual added marking with a further individual marking called from said marking list for forming a final added marking;

(7) adding said final added marking to said marking list; and (8) storing the individual added marking and the further marking, from which said final added marking has been formed, in said sub-marking memory as sub-markings of said final added marking, whereby structures of said sub-markings are preserved, wherein said coordinate comparison comprises determining a distance between a coordinate of the first adjoining marking and a coordinate of the second adjoining marking, and determining whether the distance exceeds a previously set, variable limit.

2. The method as defined in claim 1, wherein said comparing step comprises the step of comparing lengths and positions of said facing sides.

3. The method as defined in claim 1, wherein said step of determining a ratio comprises the step of determining a ratio of said overlapping area of said two adjoining individual markings with the total area of one of said two adjoining individual markings.

4. The method as defined in claim 1, wherein said combining step further comprises the step of setting a degree in combining said individual markings for providing an option to display one of individual added markings and individual markings instead of a sole final added marking.

5. The method as defined in claim 4, further comprising the steps of adding the structure of the individual markings and the individual added markings from the sub-marking memory to said marking list if one of individual added markings and individual markings are displayed instead of a sole final added marking.

6. The method as defined in claim 1, wherein said comparing and determining steps include the step of comparing coordinates in which said individual and individual added markings are positioned.

7. The method as defined in claim 1, wherein the individual markings are respective rectangles surrounding the image of a respective article.

8. The method as defined in claim 1, wherein the individual markings are displayed on the monitor screen.

9. The method as defined in claim 1, wherein the transilluminated objects are transilluminated baggage objects.

10. The method as defined in claim 1, wherein the individual markings are displayed on the monitor screen.

11. The method as defined in claim 1, wherein the transilluminated objects are transilluminated baggage objects.

12. A method of processing an X-ray image of articles contained in a transilluminated object and made visible for an observer on a monitor screen, comprising the following steps:

(a) placing individual markings about the image of certain, previously determined articles, the individual markings being displayable on the monitor screen;

(b) automatically and stepwise combining the individual markings into a final added marking if at least two individual markings mutually fit; and (c) storing said individual markings in a marking list of a memory; said combining step comprises the steps of (1) performing a coordinate comparison to identify mutually facing sides of two adjoining individual markings;

(2) determining a ratio of an overlapping area of said two adjoining individual markings to the total area of at least one of said two adjoining individual markings;

(3) forming an individual added marking from two individual markings resulting from said comparing and determining steps;

(4) storing said individual added marking in said marking list;

(5) storing said individual markings, from which said individual added marking has been formed, from said marking list in a sub-marking memory of a marking memory as sub-markings of said individual added marking;

(6) comparing said individual added marking with a further individual marking called from said marking list for forming a final added marking;

(7) adding said final added marking to said marking list; and (8) storing the individual added marking and the further marking, from which said final added marking has been formed, in said sub-marking memory as sub-markings of said final added marking, whereby structures of said sub-markings are preserved, wherein said coordinate comparison comprises determining a distance between a coordinate of the first adjoining marking and a coordinate of the second adjoining marking, and determining whether the distance exceeds a previously set, variable limit.

13. The method as defined in claim 12, wherein said comparing step comprises the step of comparing lengths and positions of said facing sides.

14. The method as defined in claim 12, wherein said step of determining a ratio comprises the step of determining a ratio of said overlapping area of said two adjoining individual markings with the total area of one of said two adjoining individual markings.

15. The method as defined in claim 12, wherein said combining step further comprises the step of setting a degree in combining said individual markings for providing an option to display one of individual added markings and individual markings instead of a sole final added marking.

16. The method as defined in claim 15, further comprising the steps of adding the structure of the individual markings and the individual added markings from the sub-marking memory to said marking list if one of individual added markings and individual markings are displayed instead of a sole final added marking.

17. The method as defined in claim 12, wherein said comparing and determining steps include the step of comparing coordinates in which said individual and individual added markings are positioned.

18. The method as defined in claim 12, wherein the individual markings are respective rectangles surrounding the image of a respective article.

* * * * *